United States Patent [19]

Mitchell et al.

[11] Patent Number: 5,705,456
[45] Date of Patent: Jan. 6, 1998

[54] HERBICIDES

[75] Inventors: Glynn Mitchell, Cookham; Stephen Christopher Smith, Netherthong, both of United Kingdom

[73] Assignee: Zeneca Limited, London, England

[21] Appl. No.: 758,537

[22] Filed: Nov. 29, 1996

[30] Foreign Application Priority Data

Dec. 1, 1995 [GB] United Kingdom ............ 9524667

[51] Int. Cl.$^6$ .................. A01N 43/76; A01N 43/78; A01N 43/50; C07D 403/04; C07D 413/04; C07D 417/04

[52] U.S. Cl. .................. 504/266; 504/270; 504/283; 540/362

[58] Field of Search ................ 540/362; 504/266, 504/270, 283

[56] References Cited

U.S. PATENT DOCUMENTS 3,818,032 6/1974 Moser et al. .............. 260/309.5

FOREIGN PATENT DOCUMENTS

| 2 212 558 | 10/1972 | Germany. |
| 1 333 464 | 10/1973 | United Kingdom. |
| 1 345 159 | 1/1974 | United Kingdom. |
| 94 13652 | 6/1994 | WIPO. |
| 95 33719 | 12/1995 | WIPO. |

*Primary Examiner*—Johann Richter
*Assistant Examiner*—Laura Lutz
*Attorney, Agent, or Firm*—Joseph R. Snyder

[57] ABSTRACT

Compounds of formula I:

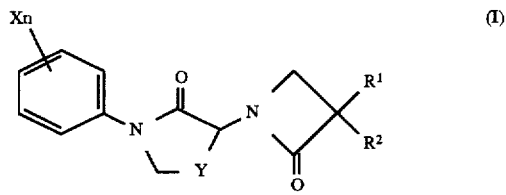

where n is 0 or an integer from 1 to 5;

X is halogen, nitro or cyano, or $C_{1-10}$ hydrocarbyl or $C_{1-10}$ hydrocarbyloxy, either of which may be substituted with one or more halogen atoms;

Y is $CH_2$, O or S; and $R^1$ and $R^2$ independently represent hydrogen, $C_{1-6}$ alkyl, $C_{1-6}$ haloalkyl, $C_{2-6}$ alkenyl, $C_{2-6}$ alkynyl or halogen;

Processes for the preparation of compounds of formula I, herbicidal compositions and methods utilising them are also disclosed.

7 Claims, No Drawings

HERBICIDES

This invention relates to chemical compounds useful as herbicides, to processes for preparing them, and to herbicidal compositions and methods utilising them.

Herbicidal compounds based upon carbonyl-substituted nitrogen containing rings are known, for example, from GB 1,345,159 and DE OS 2,212,558. WO 94/13652 and WO 95/33719 (published after the priority date of the present application) disclose various pyrrolidinone compounds which are active as herbicides.

We have now found a novel group of substituted pyrrolidinone derivatives which exhibit herbicidal activity.

According to the invention, there is provided a compound of formula I:

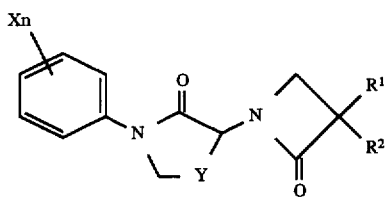

where n is 0 or an integer from 1 to 5;

X is halogen, nitro or cyano, or $C_{1-10}$ hydrocarbyl or $C_{1-10}$ hydrocarbyloxy, either of which may be substituted with one or more halogen atoms;

Y is $CH_2$, O or S; and $R^1$ and $R^2$ independently represent hydrogen, $C_{1-6}$ alkyl, $C_{1-6}$ haloalkyl, $C_{2-6}$ alkenyl, $C_{2-6}$ alkynyl or halogen.

When n is more than 1, the substituents X may be the same or different.

The expression $C_{1-10}$ hydrocarbyl in the foregoing definitions, whether the expression is used on its own or as part of a larger radical, i.e. $C_{1-10}$ hydrocarbyloxy, includes hydrocarbyl radicals of up to ten carbon atoms. Subclasses of such hydrocarbyl radicals include radicals with up to four or up to six carbon atoms. The expression $C_{1-10}$ hydrocarbyl includes within its scope aliphatic, alicyclic and aromatic hydrocarbyl groups and combinations thereof. It thus includes, for example, alkyl, alkenyl, and alkynyl radicals, cyclopropyl, cyclopropylmethyl, cyclobutyl, cyclopentyl, and cyclohexyl radicals, the adamantyl radical and the phenyl radical.

When the $C_{1-10}$ hydrocarbyl radical is substituted by one or more halogen atoms, the halogen may be chlorine, fluorine, bromine or iodine, and where more than one halogen substituent is present, the halogens may be the same or different. Preferred halogen substituents include chlorine and fluorine.

A preferred group of compounds are those in which n is an integer from 1 to 5, e.g., 1, 2 or 3.

A further preferred group of compounds are those in which X is halogen, or $C_{1-10}$ hydrocarbyl or $C_{1-10}$ hydrocarbyloxy, either of which may be substituted with one or more halogen atoms. When X is $C_{1-10}$ hydrocarbyl or $C_{1-10}$ hydrocarbyloxy particular groups it may represent include $C_{1-10}$ alkyl or $C_{1-10}$ alkoxy, more particularly $C_{1-6}$ alkyl or $C_{1-6}$ alkoxy, e.g. trifluoromethyl and trifluoromethoxy.

A further preferred group of compounds are those in which $R^1$ and $R^2$ independently represent $C_{1-6}$ alkyl, $C_{1-6}$ haloalkyl or halogen.

The formula I given above includes tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

The compounds of formula I can exist in enantiomeric or diastereomeric forms. The invention includes all individual forms and mixtures thereof in all proportions.

Particular examples of compounds of the invention are listed in Table I.

TABLE I

| Compound No | Y | Xn | $R^1$ | $R^2$ |
|---|---|---|---|---|
| 1 | $CH_2$ | 3-$OCF_3$ | Me | Me |
| 2 | $CH_2$ | 3-$OCF_3$ | Me | Cl |
| 3 | $CH_2$ | 3-$OCF_3$ | Me | $CH_2Cl$ |
| 4 | $CH_2$ | 3-$OCF_3$ | Me | Br |
| 5 | S | 3-$OCF_3$ | Me | Me |
| 6 | S | 3-$OCF_3$ | Me | Br |
| 7 | S | 3-$OCF_3$ | Me | $CH_2Cl$ |
| 8 | S | 3-$OCF_3$ | Me | Cl |
| 9 | O | 3-$OCF_3$ | Me | Me |
| 10 | O | 3-$OCF_3$ | Me | $CH_2Cl$ |
| 11 | O | 3-$OCF_3$ | Me | Br |
| 12 | O | 3-$OCF_3$ | Me | Cl |
| 13 | $CH_2$ | 3-Cl, 4-F | Me | Me |
| 14 | $CH_2$ | 3,5-diCl | Me | Me |

Note: Several of the compounds exist in two diastereoisomeric forms, these have been arbitrarily designated as Examples xA and xB, e.g. 2A and 2B, in the herbicide test results provided below.

Compounds of formula I may be prepared by a variety of processes and these form a further aspect of the invention. Compounds of formula I in which Y is $CH_2$ may be prepared for example by the process outlined in Scheme A below. In Scheme A, the symbol Ar represents the group:

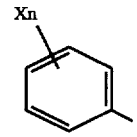

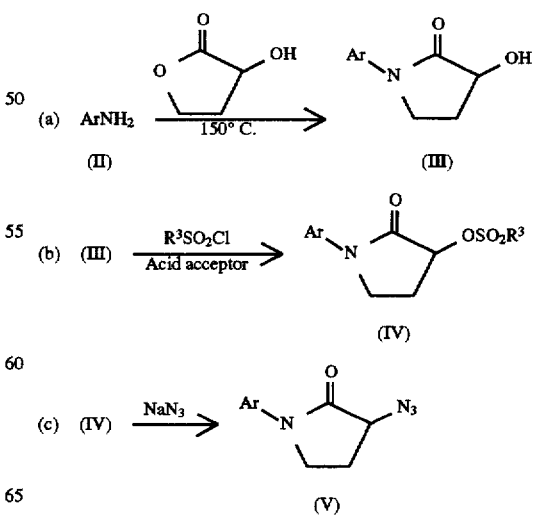

-continued
Scheme A

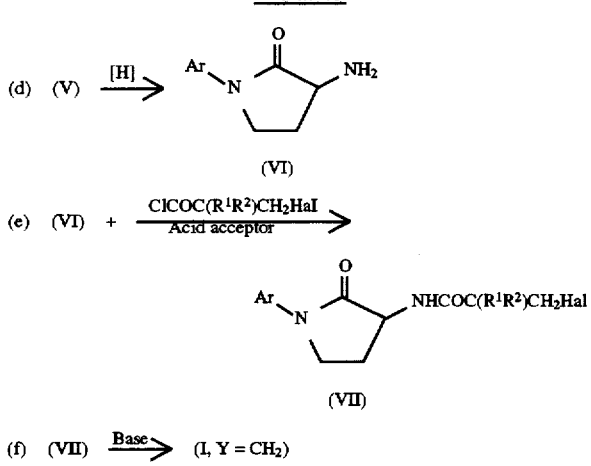

(f) (VII) $\xrightarrow{\text{Base}}$ (I, Y = CH$_2$)

According to Scheme A, an optionally substituted aniline II is reacted at elevated temperature, for example in the range 140°–200° C., preferably at about 150° C., with alphahydroxy-gammabutyrolactone to give the pyrrolidinone III. The reaction is fairly slow and may take up to 48 hours or more to go to completion. The reaction may be carried out in the presence or absence of a reaction medium or diluent. If a reaction medium is used, it must be inert towards the reactants and preferably have a boiling point in or above the range of temperature suitable for the reaction, i.e. 140°–200° C.

The hydroxy pyrrolidinone III prepared in step(a) of Scheme A is then reacted with an alkyl or arylsulfonyl chloride, e.g. methanesulfonyl chloride or p-toluene sulfonyl chloride, in the presence of an acid acceptor, e.g. a tertiary base, for example triethylamine, in a diluent or solvent for the reactants, preferably at a temperature in the range 0°–10° C. Preferably the diluent or solvent is immiscible with water. The sulfonate ester IV may then be isolated by adding water to the reaction mixture, agitating the mixture and separating the solvent from the aqueous solution. The solvent is then dried and evaporated to give the sulfonate ester IV. In step (c) of Scheme A, the sulfonate ester IV is reacted with an alkali metal azide, e.g. NaN$_3$, preferably in the presence of a solvent. The solvent may be for example a polar aprotic solvent, e.g. dimethylformamide (DMF). The reaction takes place at ambient temperature, e.g. 20°–30° C. The azido-compound V may be isolated by conventional procedures, for example by diluting the reaction mixture with water, extracting the mixture with a water-immiscible organic solvent, and drying and evaporating the organic extracts to recover the product V.

In step (d) of Scheme A, the azido-compound V is reduced to the corresponding amine VI. A variety of reducing agents may be used, for example, the azido-compound V may be treated with sodium borohydride in water or methanol, or in a mixture of water and methanol, and the amine VI isolated by extracting the reaction mixture with a water-immiscible organic solvent as described for step (c). Alternatively, the azido-compound may be treated with 1,3-propane dithiol in the presence of triethylamine, at ambient temperature, i.e. 20°–30° C. A further alternative is catalytic reduction with hydrogen in the presence of a hydrogenation catalyst, e.g. 5% palladium on charcoal.

In step (e) of Scheme A, the amine VI is reacted with an acid chloride ClCOC(R$^1$R$^2$)CH$_2$Hal, where Hal is chloro, bromo or iodo, in the presence of an acid acceptor and a diluent or solvent for the reactants to give the amide VII. The reaction is preferably carried out below ambient temperature, e.g. at 0°–10° C. The amide VII may be isolated by conventional procedures, for example by diluting the reaction mixture with saturated aqueous sodium bicarbonate solution and extracting the mixture with a water-immiscible organic solvent as described above.

In step (f) of Scheme A, the amide VII is cyclised to a compound of formula I by treatment with a base. The reaction is preferably carried out in a diluent or solvent. Examples of solvents include ethers, for example tetrahydrofuran (THF). The base may be an alkali metal hydride, for example sodium hydride. Another base that may be used is caesium fluoride, in conjunction with a tetralkylammonium salt, e.g. triethylbenzylammonium chloride, as a phase transfer catalyst. The compound of formula I, may be isolated from the reaction mixture by dilution with water and extraction with a water-immiscible organic solvent as described for step (b).

Compounds of formula I in which Y is S may be prepared by a process analogous to that outlined in steps (d) to (f) of Scheme A using as intermediates compounds analogous to compounds, V, VI and VII but wherein the CH$_2$ group of the 5-membered ring non-adjacent to the nitrogen atom is replaced by a sulphur atom. The azido-compound IX needed as starting material may be prepared as shown in Scheme B below.

Scheme B

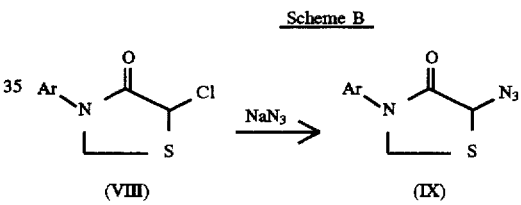

The compounds of formula VIII are known. In Scheme B the chloro-compound VIII is reacted with an alkali metal azide, e.g. sodium azide, preferably in a diluent or solvent for the reactants. Examples of solvents include dipolar aprotic solvents, for example DMF. The reaction may proceed at ambient temperature but heating to a moderate temperature, e.g. 50°–100° C., may be used to accelerate the reaction. The azido-compound IX so prepared may then be converted to an amine, following the procedure of step (d) of Scheme A. The amino compound may then be converted into an amide by reaction with ClCOC (R$^1$R$^2$)CH$_2$Hal, where Hal is chloro, bromo or iodo, and the amide cyclised by treatment with a base to produce the compound of formula I in which Y is S, following the procedures described in steps (e) and (f) respectively of Scheme A.

Compounds of formula I in which Y is O may be prepared for example by a process analogous to that outlined in steps (d) to (f) of Scheme A, but using as intermediates compounds analogous to compounds V, VI and VII, but wherein the CH$_2$ group of the 5-membered ring which is non-adjacent to the nitrogen atom of the ring is replaced by an oxygen atom. The azido-oxazolidinone XII required as starting material may be prepared by the process outlined in Scheme C below.

Scheme C

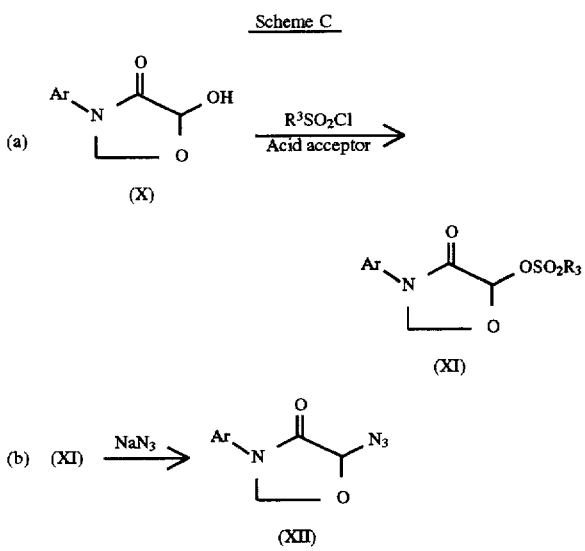

In step (a) of Scheme C the hydroxy-oxazolidinone X is treated with an alkyl- or arylsulfonyl chloride in the presence of an acid acceptor to give the sulfonate ester XI, as described in step (b) of Scheme A. In step (b) of Scheme C the sulfonate ester is reacted with an alkali metal azide to obtain the azido-oxazolidinone XII, following the procedure described in step (c) of Scheme A for making the corresponding azido pyrrolidinone V. The azido-oxazolidinone XII is then reduced to the corresponding amino compound, which is reacted with a compound ClCOC(CR$^1$R$^2$)CH$_2$Hal, where Hal is chloro, bromo or iodo, to give the corresponding amide, following the procedures of steps (d) and (e) respectively of Scheme A. The amide is then cyclised by treatment with a base to give a compound of formula I in which Y is O, following the procedure described in step (f) of Scheme A.

The hydroxy-oxazolidinone X required as starting material for Scheme C may be prepared for example by the process outlined in Scheme D below.

Scheme D

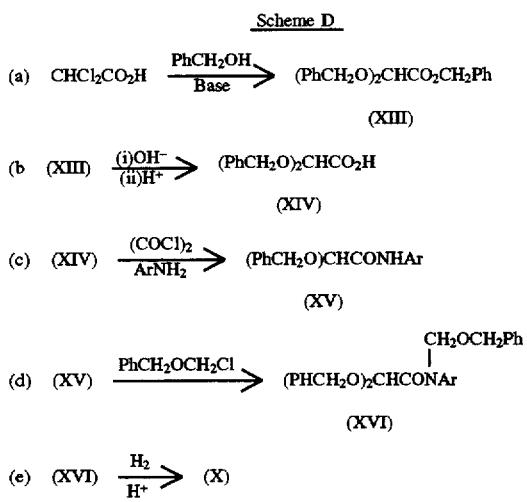

In step (a) of Scheme D, dichloracetic acid is reacted with benzyl alcohol in the presence of a base to give benzyl dibenzyloxyacetate XIII. In step (b) the benzyl ester XIII is hydrolysed with an alkali, e.g. potassium carbonate, in a suitable solvent, e.g. a mixture of water and a water miscible organic solvent e.g. THF; the reaction mixture is then acidified and the dibenzyloxyacetic acid XIV isolated by standard methods, e.g. extraction with an organic solvent. In step (c), the dibenzyloxyacetic acid XIV is converted to the corresponding acid chloride by treatment with a chlorinating agent, e.g. oxalyl chloride, preferably with a catalytic amount of DMF, and the acid chloride reacted with an optionally substituted aniline ArNH$_2$ (wherein Ar has the meaning previously ascribed to it), in the presence of an acid acceptor, e.g. a tertiary amine, and a solvent or diluent for the reactants, to give the amide XV. In step (d) of Scheme D, the amide SV is treated with benzyl chloromethyl ether in the presence of a base to give the N-benzyloxymethyl compound XVI. The reaction is preferably carried out at ambient temperature, e.g. 20°–30° C., in a two phase system of aqueous alkali, e.g. sodium hydroxide solution, and water immiscible organic solvent, e.g. dichloromethane, with a phase transfer catalyst present, e.g. tetra-butyl ammonium iodide. In step (e) of Scheme D, the N-benzyloxymethyl compound XVI is treated with hydrogen in the presence of a hydrogenation catalyst, e.g. 5% palladium on charcoal, in an acidic reaction medium to give the required compound of formula X.

Preparation of 5-hydroxy-3-aryloxazolidin-4-one intermediates

By way of example, the preparation of 5-hydroxy-3-(3-trifluoromethylphenyl)oxazolidin-4-one is described below.

a) Benzyl dibenzyloxyacetate

A solution of dichloroacetic acid (12.89 g) in benzyl alcohol (50 ml) was added to a solution of sodium benzyloxide from sodium hydride (13.53 g, 55% dispersion in mineral oil) in benzyl alcohol (150 ml). The resultant mixture was heated at 190° C. for 4 hours then the solvent distilled off under reduced pressure. The residue was triturated with ether and the solid removed by filtration and distributed between hydrochloric acid (2N) and ether. The extracts were dried (MgSO$_4$) and evaporated under reduced pressure. The residue was chromatographed on silica, using dichloromethane as eluant, to give benzyl dibenzyloxyacetate (12.50 g) as a colourless oil. None of the expected corresponding acid was eluted with more polar solvents.

NMR δ(CDCl$_3$): 4.7 (4H,dd),5.1 (1H,s), 5.2 (2H,s), 7.3 (15H,m); MS: M$^+$ 362.

NB: When the residue was triturated with ether, it appears that some of the ester product may have been lost; the work-up procedure should be modified in view of ester, rather than acid, being produced.

b) Dibenzyloxyacetic acid

Water (20 ml) and potassium carbonate (10.64 g) were added to a solution of benzyl dibenzyloxyacetate (11.15 g) in THF (80 ml) and the mixture heated under reflux for 24 hours. The mixture was allowed to cool, poured into water, extracted with ether, acidified with concentrated hydrochloric acid and again extracted with ether. The extract from acidic solution was washed with brine, dried (MgSO$_4$) and evaporated under reduced pressure to give the sub-title compound (8.12 g), which was used crude in step c).

NMR δ(CDCl$_3$): 4.7 (4H,m), 5.1 (1H,brs), 7.3 (10H,m), 9.2 (1H,brs).

c) 2,2-Dibenzyloxy-N-(3-trifluoromethylphenyl)acetamide

A stirred solution of dibenzyloxyacetic acid (4.0 g) in dichloromethane (40 ml) was cooled to 0° C. and treated dropwise with, successively, DMF (100 mg) and oxalyl chloride (2.0 g). After 30 min pyrridine (3.52 g), 3-trifluoromethyl aniline (2.64 g) and 4-dimethylaminopyridine (100 mg) were added. The mixture was stirred at 0° C. for a further 30 min then allowed to warm to room temperature. After 3 hours the mixture was poured into water, extracted with ethyl acetate and the extracts washed successively with dilute hydrochloric acid, water, aqueous sodium bicarbonate solution and brine. After drying (MgSO$_4$) the extracts were evaporated under reduced pressure to give the sub-title compound (5.62 g) as an orange gum, sufficiently pure to be used in step d).

NMR δ(CDCl$_3$): 4.7 (4H,dd), 5.1 (1H,s), 7.3 (12H,m), 7.8 (1H,dd), 7.85 (1H,s), 8.5 (1H,brs).

d) 2,2-Dibenzyloxy-N-benzyloxymethyl-N-(3-trifluoromethylphenyl)acetamide 2,2-Dibenzyloxy-N-(3-trifluoromethylphenyl)acetamide (4.75 g), benzyl chloromethylether (1.79 g) and tetrabutylammonium iodide (100 mg) were added successively to a vigorously stirred mixture of aqueous sodium hydroxide solution (100 ml, 50%) and dichloromethane (100 ml). After stirring for 18 hours the mixture was extracted several times with dichloromethane and the extracts washed with brine. After drying (MgSO$_4$) the extracts were evaporated under reduced pressure. The residue was chromatographed on silica, using hexane-ethyl acetate (4:1) as eluant, to give the sub-title compound (2.87 g).

NMR δ(CDCl$_3$): 4.6 (6H,m), 4.9 (1H,brs), 5.12 (2H,brs), 7.3 (18H,m), 7.55 (1H,dd).

e) 5-Hydroxy-3-(3-trifluoromethylphenyl)oxazolidin-4-one

A mixture of 2,2-dibenzyloxy-N-benzyloxymethyl-N-(3-trifluoromethylphenyl)acetamido (0.27 g), 10% palladium on carbon (50 mg), trifluoroacetic acid (1 ml) and dichloromethane (50 ml) was stirred under an atmosphere of hydrogen for 5 hours. The mixture was filtered through Hyflo Supercel™, evaporated under reduced pressure and chromatographed on silica, using dichloromethane-ethanol (49:1) as eluant, to give the title compound as a waxy solid (0.07 g), m.p. 75°–76° C.

NMR δ(CDCl$_3$): 5.35 (1H,brs), 5.45 (1H,d), 5.7 (2H,m), 7.5 (2H,m), 7.65 (1H,d), 7.7 (1H,s).

5-Hydroxy-3-(3-trifluoroemthoxyphenyl)oxazolidin-4-one was prepared following the above procedure but using 3-trifluoromethoxyaniline instead of 3-trifluoromethylaniline;

NMR δ(CDCl$_3$): 5.44 (1H,s), 5.65 (2H,s), 7.06–7.16 (1H,m), 7.37–7.45 (2H,m), 7.60 (1H,s).

The compounds of formula VII used as intermediates in the synthesis of compounds of formula I are novel. Therefore, according to a further aspect of the invention, there is provided a compound of formula VII;

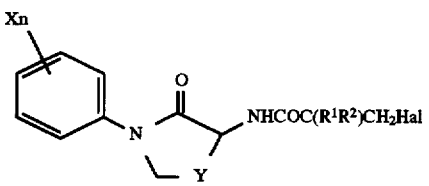

(VII)

wherein X, n, R$^1$ and R$^2$ are as defined for formula I and Hal is chloro, bromo or iodo.

The compounds of formula I above are active as herbicides, therefore according to a further aspect of the invention, there is provided a process for severely damaging or killing unwanted plants, which process comprises applying to the plants, or to the growth medium of the plants, a herbicidally effective amount of a compound of formula I as hereinbefore defined.

The compounds of formula I are active against a broad range of weed species including monocotyledonous and dicotyledonous species. They show some selectivity towards certain species; they may be used, for example, as selective herbicides in soya, maize and rice crops. The compounds of formula I may be applied directly to unwanted plants (post-emergence application) but there are preferably applied to the soil before the unwanted plants emerge (pre-emergence application).

The compounds of formula I may be used on their own to kill or severely damage plants, but are preferably used in the form of a composition comprising a compound of formula I in admixture with a carrier comprising a solid or liquid diluent.

Compositions containing compounds of formula I include both dilute compositions, which are ready for immediate use, and concentrated compositions, which require dilution before use, usually with water. Preferably the compositions contain from 0.01 to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth or gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof. The cationic agents are, for example, quaternary ammonium compounds, e.g. cetyltrimethylammonium bromide. Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl-phenol, e.g. Agral 90, or octyl-cresol.

Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s).

Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of, the concentrate. Examples of preferred suspending agents include hydrated colloidal mineral silicates, such as montmorillonite, beidellite, nontronite, hectorite, saponite and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may comprise, in addition to one or more compounds of the invention, one or more compounds not of the invention but which possess biological activity. According to a further embodiment of the invention, there is provided a herbicidal composition comprising a mixture of at least one herbicidal compound of formula I as hereinbefore defined with at least one other herbicide.

The other herbicide may be any herbicide not having the formula I, it will generally be a herbicide having a complementary action in the particular application.

Examples of useful complementary herbicides include:

A. benzo-2,1,3-thiadiazin-4-one-2,2-dioxides such as bentazone;

B. hormone herbicides and derivatives thereof e.g. salts, esters and amides, such as 2,4,5-T, 2,4-D, 2,4-DB, clopyralid, dichlorprop, dichlorprop-p, fluroxypyr, MCPA, MCPA-thioethyl, MCPB, mecoprop, mecoprop-p, pichloram, thiazopyr, and trichlopyr;

C. 1,3-dimethylpyrazole derivatives such as benzofenap, pyrazolate and pyrazoxyfen;

D. dinitrophenols and their derivatives, e.g. acetates, such as dinoterb and DNOC;

E. dinitroanilines such as dinitramine, ethalflurolin, fluchloralin, oryzalin, pendimethalin, prodiamine and trifluralin;

F. arylureas such as chlorobromuron, chlorotoluron, daimuron, dimefuron, diuron, fenuron, flumeturon, isoproturon, isourn, linuron, methabenzthiazuron, methyldymron, metobromuron, metoxuron, monolinuron, neburon and tebuthiuron;

G. phenylcarbamoyloxyphenylcarbamates such as desmedipham and phenmedipham;

H. phenylpyrazoles such as ET-751;

I. 2-phenylpyridazin-3-ones such as chloridazon and norflurazon;

J. pyridones such as fluridone;

K. pyrimidinyloxybenzoic herbicides such as DPX-PE350 (pyrithiobac-sodium) and KIH-2023 (bispyribac-sodium);

L. uracil herbicides such as bromacil, lenacil and terbacil;

M. triazines such as amytryn, atrazine, cyanazine, dimethametryn, prometon, prometryn, propazine, simazine, simetryne terbuthylazine, terbutryn and trietazine;

N. triazoles such as amitrole;

O. triazolinones such as carfentriazone (F-8426) and sulfentriazone (F-6285);

P. phosphorothioates such as bensulide, butamifos and piperophos;

Q. phthalamides such as flumioxazin;

R. thiocarbamates such as butylate*, cycloate, dimepiperate, EPTC*, esprocarb, molinate, orbencarb, pebulate, prosulfocarb, thiobencarb, tiocarbazil, triallate and vernolate;

* These compounds are preferably employed in combination with a safener such as AD-67, benoxacor, cloquintocet-methyl, dichlormid, fenchlorazole-ethyl, fenclorim, fluxofenim, furilazole, MG-191, naphthalic anhydride, oxabentrinil or R-29148.

S. 1,2,4-triazin-5-ones such as metamitron and metribuzin;

T. benzoic acid herbicides such as 2,3,6-TBA, chloramben and dicamba;

U. chloroacetanilides such as acetochlor, alachlor, butachlor, dimethachlor, dimethanamid, metazachlor, metolachlor, pretilachlor, propachlor, propanil and thenylchlor (NSK-850);

V. dihalobenzonitriles such as bromoxynil, dichlobenil, ioxymil and the dihalobenzonitrile herbicade precursor bromofenoxim;

W. haloalkanoic herbicides such as TCA and salts thereof and dalapon;

X. diphenylethers such as aciflurofen and salts and esters thereof, aclonifen, bifenox, chlornethoxyfen, chlornitrofen, fluroglycofen and salts and esters thereof, formesafen and lactofen;

Y. diphenylureas such as oxyfluorfen;

Z. phenoxyphenoxypropionates such as clodinafop-propargyl, cyhalofop-butyl (DEH-112), diclofop and esters thereof e.g. the methyl ester, fenoxaprop and esters thereof e.g. the ethyl ester, fluazifop and esters thereof, haloxyfop and esters thereof, propaquizafop, quiazolfop and esters thereof and quizalofop-p-tefuryl;

AA. cyclohexanediones such as alloxydim and salts thereof, butroxydim, clethodim, cycloxydim, sethoxydim and tralkoxydim;

BB. sulfonyl ureas such as amidosulfuron, azimsulfuron, benzsulfuron and esters thereof such as DPX-M6313, chlorimuron and esters thereof such as the ethyl ester, chlorosulfuron, cinosulfuron, ethametsulfuron-methyl, flazasulfuron, halosulfuron, HOE-95404, imazosulfuron, metsulfuron and esters thereof, nicosulfuron, pirimisulfuron and esters thereof such as the methyl ester, prosulfuron, pyrazosulfuron, rimsulfuron, sulfometuron, thifensulfuron, triasulfuron, tribenuron, tribenuron-methyl and triflusulfuron-methyl;

CC. imidazolidinones such as imazamethabenz, imazapyr and isopropylammonium salts thereof, imazaquin and imazethapyr;

DD. methyl isothiocyanate herbicide precursors such as dazomet;

EE. arylanilides such as diflufenican, flamprop, flamprop-M and esters thereof;

FF. quinolinecarboxylic acids such as quimerac and quinclorac;

GG. amino acid herbicides such as bialaphos, glyphosate and glufosinate and their salts and esters and sulphosate;

HH. organoarsenical herbicides such as DSMA and monosodium methanearsonate (MSMA);

II. organophosphorus herbicides such as anilofos and fosamine-ammonium;

JJ. herbicidal amide derivatives such as bromobutide, carbetamide, FOE-5043, isoxaben, napropamide, naproanilide, naptalam, propyzamide and tebutam;

KK. sulfamoylureas such as AC-322,140 (cyclosulfamuron);

LL. sulfonanilides such as chloransulam-methyl, DE-511 (metosulam) and flumetsulan;

MM. carbamates such as chlorpropham;

NN. triketones such as sulcotrione;

OO. miscellaneous herbicides such as ammonium sulfamate, asulam, benazolin, cinmethylin, clomazone, difenzoquat and salts thereof e.g. the methyl sulphate salt, dimethipin, diphenamid, dithiopyr, ethofumesate, fumiclorac, flupoxam, flurenol-butyl, flurochloridone, flurtamone, hexazinone, HW-32, KIH-9201 (fluthiacetmethyl), KPP-314, mefenacet, oxidiazon, pyridate, RPA-201772 (isoxaflutole), sodium chlorate and thidiazimin; and PP. contact herbicides including bipyridylium herbicides such as diquat and paraquat;

The invention is illustrated by the following Examples. The abbreviations used in the Examples have the following meanings:

NMR spectrum: nuclear magnetic resonance spectrum which were recorded at 270 or 400 MHz. (This refers to the proton magnetic resonance spectrum recoreded in CDCl$_3$ unless otherwise stated).

Example 1

1-[1-(3-Trifluoromethyoxyphenyl)pyrrolidin-2-one-3-yl]-3, 3-dimethylazetidin-2-one a) 1-(3-Trifluoromethoxyphenyl)-3-hydroxy-2-pyrrolidinone A mixture of alpha-hydroxy-gamma-butyrolactone (22.0 g) and 3-trifluoromethoxy aniline (19.0 g) was heated to 150° C. (bath temperature) for 48 hours. The mixture was allowed to cool and poured into a mixture of diethyl ether and water. After shaking, the ether layer was separated and the aqueous layer extracted with diethyl ether (x2). The combined ether extracts were washed with 2M hydrochloric acid, water and brine, then dried (MgSO$_4$). The mixture was evaporated under reduced pressure to leave an oil, which on trituration with a mixture of diethyl ether/hexane gave the sub-title compound as an off-white solid (19.42 g).

NMR δ: 2.12 (1H,m), 2.62 (1H,m), 3.50 (1H,br s), 3.70–3.88 (2H,m), 4.51 (1H,t), 7.05 (1H,m), 7.41 (1H,t), 7.58 (1H,m), 7.62 (1H,m).

b) 1-(3-Trifluoromethoxyphenyl)-3-methanesulfonyloxy-2-pyrrolidinone

A stirred solution of 1-(3-trifluoromethoxyphenyl)-3-hydroxy-2-pyrrolidone (19.42 g) in dichloromethane (250 ml) was cooled in an ice bath and treated with triethylamine (11.32 ml). Methanesulfonyl chloride (6.05 ml) was added dropwise via a syringe, and the mixture stirred with cooling for a further 1 hour after which it was allowed to warm to room temperature. After stirring for 2 hours at room temperature methanesulfonyl chloride (0.5 ml) and triethylamine (1.0 ml) were added and the mixture was stirred for a further 2 hours. The reaction mixture was poured into water and extracted with dichloromethane. The dichloromethane extracts were washed with water, dried (MgSO$_4$) and the solvent evaporated under reduced pressure to give the crude sub-title compound (23.0 g), which was used without further purification.

c) 3-Azido-1-(3-trifluoromethoxyphenyl)-2-pyrrolidinone

A stirred solution of crude 1-(3-trifluoromethoxyphenyl)-3-methanesulfonyloxy-2-pyrrolidinone (4.00 g) in DMF (15 ml) was treated with sodium azide (0.76 g) and the mixture stirred for 16 hours. The mixture was poured into water and extracted with diethyl ether (x2). The combined ether extracts were washed with water (x3) and brine, then dried (MgSO$_4$). Evaporation of the solvent under reduced pressure gave the crude sub-title compound (3.50 g), which was used without further purification.

NMR δ: inter alia 2.04 (1H,m), 2.52 (1H,m), 3.71–3.90 (2H,m), 4.32 (1H,t), 7.04 (1H,m), 7.39 (1H,t), 7.55 (1H,m), 7.65 (1H,m).

d) 3-Amino-1-(3-trifluoromethoxyphenyl)-2-pyrrolidinone

A stirred solution of crude 3-azido-1-(3-trifluoromethoxyphenyl)-2-pyrrolidinone (3.50 g) in 1,3-propanedithiol (10 ml) was treated with triethylamine (4 ml). The solution was stirred for 16 hours then poured into water. The resultant mixture was extracted with diethyl ether (x3), the combined ether extracts washed with brine and dried (MgSO$_4$). Evaporation of the solvent under reduced pressure left a yellow oil which was separated by chromatography on silica-gel, eluting with ethyl acetate followed by a 1:1 mixture of ethyl acetate and methanol, to give the sub-title compound as a clear solid (2.24 g).

NMR δ: 1.88 (1H,m), 2.59 (1H,m), 3.65–3.80 (3H,m), 7.01 (1H,m), 7.38 (1H,t), 7.56 (1H,dd), 7.65 (1H,m).

e) 1-(3-Trifluoroemthoxyphenyl)-3-(3-chloro-2,2-dimethylpropanoyl)amino-2-pyrrolidinone A stirred solution of 3-amino-1-(3-trifluoromethoxyphenyl)-2-pyrrolidinone (0.30 g) and triethylamine (0.4 ml) in dichloromethane (10 ml) was cooled in an ice-bath and treated dropwise with 3-chloro-2,2-dimethylpropanoyl chloride (0.2 ml). The solution was stirred for 1 hour then poured into saturated aqueous sodium bicarbonate. The mixture was extracted with dichloromethane (x3), the combined extracts dried (MgSO$_4$) and evaporated under reduced pressure. The residue was purified by filtration through a silica pad, washing through with 1:1 ethyl acetate/hexane. The crude product was recrystallized from acetate/hexane to give the sub-title compound as a solid.

NMR δ: 1.35 (6H,s), 1.92 (1H,m), 2.93 (1H,m), 3.59 (1H,d), 3.69 (1H,d), 3.80–3.88 (2H,m), 4.51 (1H,m), 6.48 (1H,brd), 7.04 (1H, m), 7.40 (1H,t), 7.52 (1H,m), 7.70 (1H, m).

f) 1-[1-(3-Trifluoromethoxyphenyl)pyrrolidin-2-one-3-yl]-3,3-dimethylazetidin-2-one A stirred solution of 1-(3-trifluoromethoxyphenyl)-3-(3-chloro-2,2-dimethylpropanoyl)amino-2-pyrrolidinone (0.31 g) in THF (5 ml) was treated with a 60% dispersion of sodium hydroxide in oil (0.036 g). Once the effervescence had ceased, the yellow mixture was stirred for 5 min then poured into water. The mixture was extracted with dichloromethane (x2), the combined extracts were washed with brine and dried (MgSO$_4$). Evaporation of the solvent under reduced pressure left an oil, which was purified by chromatography on silica-gel, eluting with ethyl acetate/hexane mixtures, to give the title compound as a pale tan crystalline solid (0.20 g).

NMR δ: 1.35 (3H,s), 1.39 (3H,s) 2.29 (1H,m), 2.52 (1H,m), 3.28 (1H,d), 3.23 (1H,d), 3.72–3.91 (2H,m), 4.61 (1H,dd), 7.04 (1H,m), 7.39 (1H,t), 7.52 (1H,dd), 7.68 (1H, m).

Example 2

1-[1-(3-Trifluoromethoxyphenyl)pyrrolidin-2-one-3-yl]-3-chloro-3-methylazetidin-2-one a) 1-(3-Trifluoromethoxyphenyl)-3-(2,3-dichloro-2-methylpropanoyl)amino-2-pyrrolidinone The procedure of Example 1e) gave the sub-title compound as a 1:1 mixture of diastereomers.

NMR δ: inter alia 2.37 (3H,s), 2.39 (3H,s) [methyl signals for diastereomers], 4.47 (1H,m), 4.59 (1H,m) [pyrrolidinone 3-H resonances for diastereomers].

b) 1-[1-(3-Trifluoromethoxyphenyl)pyrrolidin-2-one-3-yl]-3-chloro-3-methylazetidin-2-one A stirred solution of 1-(3-trifluoromethoxyphenyl)-3-(2, 3-dichloro-2-methylpropanoyl)amino-2-pyrrolidinone (0.82 g) in THF (10 ml) was treated with caesium fluoride (1.29 g) followed by benzyltriethyl ammonium chloride (0.09 g). The mixture was heated under reflux, cooled and poured into water. The resultant mixture was extracted with chloroform (x3) and the combined extracts dried (Na$_2$SO$_4$). Evaporation of the solvent under reduced pressure left an oil which was purified by chromatography on silica-gel, eluting with ethyl acetate/hexane mixtures, to give the title compound as a mixture of diastereomers:

Compound 2A (0.135 g);

NMR δ: 1.89 (3H,s), 2.05 (1H,m), 2.22 (1H,m), 2.60 (1H,m), 2.78–2.90 (3H,m), 4.35 (1H,dd), 7.05 (1H,m), 7.41 (1H,t), 7.52 (1H,dd), 7.63 (1H,m).

Compound 2B (0.124 g);

NMR δ: 1.90 (3H,s) 2.05 (1H,m), 2.42–2.65 (2H,m), 3.68–3.95 (3H,m), 4.42 (1H,dd), 7.05 (1H,m), 7.39 (1H,t), 7.51 (1H,dd), 7.63 (1H,m).

Example 3

1-[1-(3-Trifluoromethoxyphenyl)pyrrolidin-2-one-3-yl]-3-chloromethyl-3-methylazetidin-2-one a) 2,2-Bis(chloromethyl)propanoyl chloride DMF (1 drop) was added to a solution of 2,2-bis(chloromethyl)propanoic acid (1.4 g) in DCM (1.5 ml), the solution was cooled to 0° C. and oxalyl chloride (0.75 ml) added. After gas evolution had stopped the mixture was concentrated in vacuo to give the sub-title compound as a yellow oil (1.51 g) which was used directly in the next step.

b) 1-(3-Trifluoromethoxyphenyl)-3-[2,2-bis(chloromethyl) propanoyl]amino-2-pyrrolidinone The procedure of Example 1e) gave the sub-title compound as a mixture of rotamers.

NMR δ: inter alia 1.45 (3H,s), 4.50 (1H,m).

c) 1-[1-(3-Trifluoromethoxyphenyl)pyrrolidin-2-one-3-yl]-3-chloromethyl-3-methylazetidin-2-one The procedure of Example 1f) gave the title compound as a mixture of diastereomers:

Compound 3A; m.p. 104°–106° C.;

NMR δ: 1.50 (3H,s), 2.20–2.34 (1H,m), 2.50–2.60 (1H, m), 3.20+3.50 (2H,2xd), 3.62+3.75 (2H,2xd), 3.80 (2H,m), 4.65 (1H,m), 7.05 (1H,m), 7.40 (1H,t), 7.52 (1H,m), 7.70 (1H,s).

Compounds 3B; m.p. 107°–109° C.;

NMR δ: 1.45 (3H,s), 2.25–2.40 (1H, m), 2.50–2.60 (1H, m), 3.20–3.50 (2H,2xd), 3.65+3.80 (2H,2xd), 3.80 (2H,m), 4.50 (1H,m), 7.05 (1H,m), 7.40 (1H,t), 7.52 (1H,m), 7.70 (1H,s).

Example 4

1-[1-(3-Trifluoroemthoxyphenyl)pyrrolidin-2-one-3-yl]-3-bromo-3-methylazetidin-2-one a) 1-(3-Trifluoromethoxyphenyl)-3-(2,3-dibromo-2-methylpropanoyl)amino-2-pyrrolidinone The procedure of Example 1e) gave the sub-title compound as a 1:1 mixture of diasteroemers, m.p. 115°–119° C.

NMR δ: inter alia 2.00–2.15 (3H,s) [methyl signals for diastereomers], 4.40–4.60 (1H,m) [pyrrolidinone 3-H resonances for diastereomers].

b) 1-[1-(3-Trifluoromethoxyphenyl)pyrrolidin-2-one-3-yl]-3-bromo-3-methylazetidin-2-one The procedure was Example 1f) gave the title compound as a mixture of diasteroemers:

Compound 4A; m.p. 111°–113° C.;

NMR δ: 2.00 (3H,s), 2.15–2.30 (1H,m), 2.50–2.65 (1H, m), 3.65–3.90 (4H,m), 4.70–4.80 (1H,m), 7.00–7.10 (1H, m), 7.40 (1H,t), 7.50 (1H,m), 7.68 (1H,s).

Compound 4B; m.p. 93°–94° C.;

NMR δ: 1.95 (3H,s), 2.40–2.65 (2H,m), 3.70+3.90 (4H, m), 4.40–4.50 (1H,t), 7.05 (1H,d), 7.40 (1H,t), 7.50 (1H,m), 7.68 (1H,s).

Example 5

1-[3-(3-Trifluoromethoxyphenyl)thiazolidin-4-one-5-yl]-3, 3-dimethylazetidin-2-one a) 5-Azido-3-(3-trifluoromethoxyphenyl)thiazolidin-4-one Sodium azide (2.78 g) was added to a solution of 5-chloro-3-(3-trifluoromethoxyphenyl)thiazolidin-4-one (7.50 g) in DMF (50 ml). After 2 hours the mixture was poured into water, extracted with ethyl acetate (x3), dried (MgSO$_4$) and concentrated in vacuo to give the sub-title compound (5.40 g), which was used directly in the next step.

b) 5-Amino-3-(3-trifluoroemthoxyphenyl)thiazolidin-4-one

The procedure of Example 1d) gave the sub-title compound as a yellow solid.

NMR δ: 2.10–2.20 (2H,br s), 4.65–4.75+4.78–4.86 (2H, 2xd), 5.08 (1H,s), 7.10 (1H,s), 7.40+7.45 (2H,m), 7.50 (1H,s).

c) 5-(3-Chloro-2,2-dimethylpropanoyl)amino-3-(3-trifluoromethoxyphenyl)thiazolidin-4-one The procedure of Example 1e) gave the sub-title compound as a cream solid, m.p. 130°–132° C.

d) 1-[3(3-Trifluoromethoxyphenyl)thiazolidin-4-one-5-yl]-3,3-dimethylazetidin-2-one The procedure of Example 1f) gave the title compound (0.171 g);

NMR δ: 1.30–1.35 (6H,2xs), 3.12–3.28 (2H,2xd), 4.75+ 5.90 (2H,2xd), 5.75 (1H,s), 7.15 (1H,m), 7.45 (3H,m).

Example 6

1-[3-(3-Trifluoromethoxyphenyl)thiazolidin-4-one-5-yl]-3-bromo-3-methylazetidin-2-one a) 5-(2,3-Dibromo-2-methylpropanoyl)amino-3-(3-trifluoromethoxyphenyl)thiazolidin-4-one The procedure of Example 1e) gave the sub-title compound, m.p. 90°–96° C.

NMR δ: 2:05 (3H,2xs), 3.9 (2H,s), 4.75+5.05 (2H,m), 5.61–5.75 (1H,2xm), 7.15 (1H,m), 7.4–7.5 (3H,m).

b) 1-[3-(3-Trifluoromethoxyphenyl)thiazolidin-4-one-5-yl]-3-bromo-3-methylazetidin-2-one The procedure of Example 1f) gave the title compound as a mixture of diastereomers, m.p. 111°–113° C.;

NMR δ: 1.9 (3H,s), 3.7–3.8 (2H,m), 4.75–5.00 (2H,2xm), 5.65 (1H,s), 7.15 (1H,m), 7.40–7.50 (3H,m).

Example 7 b) 1-[3-(3-Trifluoromethoxyphenyl)thiazolidin-4-one-5-yl]-3-chloromethyl-3-methylazetidin-2-one a) 5-[2,2-Bis(chloromethyl)propanoyl]amino-3-(3-trifluoromethoxyphenyl)thiazolidin-4-one The procedure of Example 1e) gave the sub-title compound, m.p. 90°–96° C.

b) 1-[3-(3-Trifluoromethoxyphenyl)thiazolidin-4-one-5-yl]-3-chloromethyl-3-methylazetidin-2-one The procedure of Example 1f) gave the title compound as a mixture of diastereomers:

Compound 7A;

NMR δ: 1.4 (3H,s), 3.3–3.45 (2H,2xd), 3.6–3.8 (2H,2xd), 4.7–4.95 (2H,2xd), 5.7 (1H,s), 7.15 (1H,m), 7.45 (3H,m).

Compound 7B;

NMR δ: 1.45 (3H,s), 3.15–3.55 (2H,2xd), 3.6–3.75 (2H, 2xd), 4.8–4.9 (2H,2xd), 5.8 (1H,s), 7.15 (1H, m), 7.45 (3H,m).

Example 8

1-[3-(3-Trifluoromethoxyphenyl)thiazolidin-4-one-5-yl]-3-chloro-3-methylazetidin-2-one a) 5-(2,3-Dichloro-2-methoxypropanoyl)amino-3-(3-trifluoromethoxyphenyl)thiazolidin-4-one The procedure of Example 1e) gave the sub-title compound.

b) 1-[3-(3-Trifluoromethoxyphenyl)thiazolidin-4-one-5-yl]-3-chloromethyl-3-methylazetidin-2-one The procedure of Example 2b) gave the title compound as a mixture of diastereomers:

Compound 8A;

NMR δ: 1.88 (3H, s), 3.45 (1H,d), 3.75 (1H,d), 4.75–4.88 (2H,m), 5.90 (1H,s), 7.15 (1H,m), 7.40–7.56 (3H,m);

MS: EI 380 (M$^+$), CI381 (MH$^+$), 398 (MNH$_4^+$).

Compound 8B;

NMR δ: 1.83 (3H,s), 3.69 (2H,m), 4.76 (1H,d), 4.76 (1H,d), 5.00 (1H,d), 5.61 (1H,s), 7.16 (1H,m), 7.40–7.50 (3H,m);

MS: EI 380 (M$^+$), CI381 (MH$^+$), 398 (MNH$_4^+$).

Example 9

1-[3-(3-Trifluoromethoxyphenyl)oxazolidin-4-one-5-yl]-3,3-dimethylazetidin-2-one a) 5-Chloro-3-(3-trifluoromethoxyphenyl)oxazolidin-4-one Oxalyl chloride (2.7 ml) was added dropwise over 1 min to a stirred solution of 5-hydroxy-3-(3-trifluoromethoxyphenyl)oxazolidin-4-one (8.17 g) in DCM (60 ml) containing DMF (1 drop) at 0° C. The mixture was allowed to warm to room temperature and once gas evolution had stopped the solvent was removed in vacuo to give the sub-title compound (8.5 g) which was used directly in the next step.

b) 5-Azido-3-(3-trifluoromethoxyphenyl)oxazolidin-4-one

The procedure of Example 5a) gave the sub-title compound.

c) 5-Amino-3-(3-trifluoromethoxyphenyl)oxazolidin-4-one

The procedure of Example 1d) gave the sub-title compound.

d) 5-(3-Chloro-2,2-dimethylpropanoyl)amino-3-(3-trifluoromethoxyphenyl)oxazolidin-4-one The procedure of Example 1c) gave the sub-title compound as a cream solid, m.p. 135°–139° C.

NMR δ: 1.35 (6H,d), 4.10 (2H,ABq), 5.45 (1H,s), 5.58 (2H,m), 7.05–7.60 (5H,m).

e) 1-[3-(3-Trifluoromethoxyphenyl)oxazolidin-4-one-5-yl]-3,3-dimethylazetidin-2-one The procedure of Example 1f) gave the title compound.

NMR δ: 1.35 (6H,2xs), 3.25 (2H,m), 5.40+5.55 (2H, 2xm), 5.70 (1H,s), 7.10 (1H,d), 7.40 (2H,m), 7.65 (1H,s);

MS: EI 344 (M$^+$), CI345 (MH$^+$), 362 (MNH$_4^+$).

Example 10

1-([3-(3-Trifluoromethoxyphenyl)oxadolidin-4-one-5-yl]-3-chloromethyl-3-methylazetidin-2-one a) 5-[2,2-Bis(chloromethyl)propanoyl]amino-3-(3-trifluoromethoxyphenyl)oxazolidin-4-one The procedure of Example 1e) gave the sub-title compound, m.p. 140°–143° C.

NMR δ: 1.45 (3H,s), 3.75 (4H,m), 5.40+5.50 (2H,2xm), 5.65 (1H,m), 7.05 (1H,d), 7.40–7.45 (2H,m), 7.5–7.6 (2H, 2xm);

MS: EI 414 (M$^+$), CI 415 (MH$^+$), 432 (MNH$_4^+$).

b) 1-[3-(3-Trifluoromethoxyphenyl)oxazolidin-4-one-5-yl]-3-chloromethyl-3-methylazetidin-2-one The procedure of Example 1f) gave the title compound as a mixture of diastereomers:

Compounds 10A;

NMR δ: 1.50 (3H,s), 3.26 (1H,d), 3.57 (1H,d), 3.62 (1H,d), 3.79 (1H,d), 5.45 (1H,d), 5.55 (1H,d), 5.73 (1H,s), 7.12 (1H,m), 7.38–7.48 (2H,m), 7.60 (1H,s);

MS: EI 378 (M$^+$), CI 379 (MH$^+$), 396 (MNH$_4^+$).

Compound 10B;

NMR δ: 1.48 (3H,s), 3.24 (1H, d), 3.58 (1H,d) 3.62 (1H, d), 3.80 (1H,d), 5.45 (1H,d), 5.54 (1H,d), 5.65 (1H,s), 7.10 (1H,m), 7.38–7.48 (2H,m), 7.60 (1H,s);

MS: EI 378 (M$^+$), CI 379 (MH$^+$), 396 (MNH$_4^{3o}$).

Example 11

1-[3-(3-Trifluoromethoxyphenyl)oxazolidin-4-one-5-yl]-3-bromo-3-methylazetidin-2-one a) 5-(2,3-Dibromo-2-methylpropanoyl)amino-3-(3-trifluoromethoxyphenyl)oxazolidin-4-one The procedure of Example 1e) gave the sub-title compound as a mixture of diastereomers as a yellow solid, m.p. 100°–105° C.

NMR δ: 2.05 (3H,2xs), 3.9 (2H,m), 5.45 (1H,m), 5.6 (2H,m), 7.1 (1H,m), 7.4–7.4 (2H,m), 7.6 (1H,s).

b) 1-[3-(3-Trifluoromethoxyphenyl)oxazolidin-4-one-5-yl]-3-bromo-3-methylazetidin-2-one The procedure of Example 1f) gave the title compound as a mixture of diastereomers:

Compound 11A;

NMR δ: 1.97 (3H,s), 3.68 (1H,d), 3.81 (1H,d), 5.48 (1H,d), 5.53 (1H,dd), 5.79 (1H,brs), 7.11 (1H,m), 7.35–7.50 (2H,m), 7.60 (1H, brs);

MS: EI 408 (M$^+$), CI 411 (MH$^+$), 428 (MNH$_4^+$).

Compound 11B;

NMR δ: 1.95 (3H,s), 3.70 (1H,d), 3.88 (1H,d), 5.56 (1H,d), 5.67 (1H,dd), 5.62 (1H,d), 7.12 (1H,m), 7.37–7.49 (2H,m), 7.61 (1H,brs);

MS: EI 408 (M$^+$), CI411 (MH$^+$), 428 (MNH$_4^+$).

Example 12

1-[3-(3-Trifluoromethoxyphenyl)oxazolidin-4-one-5-yl]-3-chloro-3-methylazetidin-3-one a) 5-(2,3-Dichloro-2-methylpropanoyl)amino-3-(3-trifluoromethoxyphenyl)oxazolidin-4-one The procedure of Example 1e) gave the sub-title compound as a mixture of diastereomers, m.p. 129°–136° C.

NMR δ: 1.85 (3H,2xs), 3.75+4.05 (2H,2xm), 5.45–5.7 (3H,m), 7.1 (1H,m), 7.4 (2H,m), 7.6 (1H,s), 7.75 (1H,brm).

b) 1-[3-(3-Trifluoromethoxyphenyl)oxazolidin-4-one-5-yl]-3-chloromethyl-3-methylazetidin-2-one The procedure of Example 2b) gave the title compound as a mixture of diastereomers:

Compound 12A;

NMR δ; 1.82 (3H,s), 3.6+3.72 (2H,2xd), 5.45+5.55 (2H, 2xm), 5.80 (1H,s), 7.12 (1H,m), 7.35–7.50 (2H,m), 7.65 (1H,s).

Compound 12B;

NMR δ: 1.82 (3H,m), 3.6+3.75 (2H,2xd), 5.45+5.55 (2H,2xm), 5.65 (1H,s), 7.12 (1H,m), 7.35–7.50 (2H,m), 7.65 (1H,s).

Example 13

1-[1-(3-Chloro-4-fluorophenyl)pyrrolidin-2-one-3-yl]-3,3-dimethylazetidin-2-one a) 3-Azido-1-(3-chloro-4-fluorophenyl)-2-pyrrolidinone Sodium azide (0.45 g) was added to a solution of 3-bromo-1-(3-chloro-4-fluorophenyl)-2-pyrrolidinone (2.00 g) in DMF (16 ml) and the mixture left to stand overnight. A further portion of sodium azide (0.15 g) was added and the mixture again left to stand overnight. The mixture was poured into water giving a white solid which was isolated by filtration, dissolved in ether, dried (MsSO$_4$) and concentrated in vacuo to give the sub-title compound as an off-white solid (2.10 g) which was used directly in the next step.

NMR δ: 2.05 (1H,m), 2.55 (1H,m), 3.80 (2H,m), 4.35 (1H,t), 7.15 (1H,t), 7.51 (1H,m), 7.80 (1H,m).

b) 3-Amino-1-(3-chloro-4-fluorophenyl)-2-pyrrolidinone

The procedure of Example 1d) gave the sub-title compound as a white solid, m.p. 111°–112° C.

NMR δ: 1.85 (2H,s), 1.90 (1H,m), 2.60 (1H,m), 3.72 (3H,m), 7.15 (1H,t), 7.50 (1H,m), 7.78 (1H,dd).

c) 1-(3-Chloro-4-fluorophenyl)-3-(3-chloro-2,2-dimethylpropanoyl)amino-2-pyrrolidinone The procedure of Example 1e) gave the sub-title compound as a white solid, m.p. 151°–152° C.

NMR δ: 1.35 (6H,s), 2.00 (1H,m), 2.93 (1H,m), 3.65 (2H,dd), 3.82 (2H,m), 4.50 (1H,m), 6.45 (1H,brd), 7.15 (1H,m), 7.50 (1H,m), 7.80 (1H,m).

d) 1-[1-(3-Chloro-4-fluorophenyl)pyrrolidin-2-one-3-yl]-3,3-dimethylazetidin-2-one The procedure of Example 1f) gave the title compound as a white solid, m.p. 120°–121° C.

NMR δ: 1.35 (3H,s), 1.40 (3H,s), 2.28 (1H,m), 2.52 (1H,m), 3.18 (1H,d), 3.22 (1H,d), 3.80 (1H,m), 4.60 (1H, dd), 7.12 (1H,dd), 7.50 (1H,m), 7.80 (1H,dd).

Example 14

1-[1-(3,5-Dichlorophenyl)pyrrolidin-2-one-3-yl]-3,3-dimethylazetidin-2-one a) 3-Azido-1-(3,5-dichlorophenyl)-2-pyrrolidinone The procedure of Example 13a) gave the sub-title compound as a red oil.

NMR δ: 2.00 (1H,m), 2.50 (1H,m), 3.80 (2H,m), 4.33 (1H,dd), 7.15 (1H,t), 7.60 (2H,d).

b) 3-Amino-1-(3,5-dichlorophenyl)-2-pyrrolidinone

The procedure of Example 1d) gave the sub-title compound as an off-white solid, m.p. 162°–163° C.

NMR δ: 1.80 (2H,brs), 1.90 (1H,m), 2.60 (1H,m), 3.72 (3H,m), 7.15 (1H,t), 7.60 (2H,d).

c) 1-(3,5-Dichlorophenyl)-3-(3-chloro-2,2-dimethylpropanoyl)amino-2-pyrrolidinone The procedure of Example 1e) gave the sub-title compound as a white solid, m.p. 149°–150° C.

NMR δ: 1.35 (6H,s), 2.00 (1H,m), 2.90 (1H,m), 3.65 (2H,dd), 3.80 (2H,m), 4.50 (1H,m), 6.50 (1H,brd), 7.20 (1H,t), 7.62 (2H,d).

d) 1-[1-(3,5-Dichlorophenyl)pyrrolidin-2-one-3-yl]-3,3-dimethylazetidin-2-one

The procedure of Example 1f) gave the title compound as a white solid, m.p. 185°–186° C.

NMR δ: 1.35 (3H,s), 1.40 (3H,s), 2.25 (1H,m), 2.55 (1H,m), 3.18 (1H,d), 3.22 (1H,d), 3.80 (2H,m), 4.60 (1H, dd), 7.18 (1H,t), 7.62 (2H,d).

Biological Data

The herbicidal activity of the compounds was tested as follows:

Sample Preparation

Each compound was dissolved in an appropriate amount, dependent on the final spray volume, of a solvent/surfactant blend comprising 16.7 g/liter of Tween 85 and 33.3 g/liter of Synperonic NPE-1800 dissolved in cyclohexanone. [Tweed 85 is a Trade Mark for a surface-active agent comprising 20 moles polyoxyethylene sorbitan trioleate. Synperonic NPE-1800 is a Trade Mark for a surface-active agent comprising propoxylated and ethoxylated nonylphenol derivative]. If the chemical did not dissolve glass beads were added and the mixture was shaken to effect dissolution or suspension of the chemical after which the beads were removed. In all cases, the mixture was then diluted to the required spray volume. The final spray volume was dependent on the species range and the application mode (i.e. post-emergence, pre-emergence or both), typical spray volumes were in the range of from 6 to 18 ml. The sprayed aqueous emulsion contained 4% of the initial solvent/surfactant mix and the test chemical at an appropriate concentration.

Test Methods a) Pre-emergence

To detect pre-emergence herbicidal activity, crop seeds were sown at 2 cm depth and weeds seeds at 1 cm depth beneath compost and sprayed with the test samples prepared as described above at a rate of 400 liters per hectare. 20 days after spraying, the seedlings in sprayed trays were compared with the seedlings in unsprayed control trays. Damage to plants was assessed on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100%

The results of the pre-emergence tests are given in Table II below.

b) Post-flood, post-emergence in rice paddy

To detect herbicidal activity in post-flood, post-emergence conditions in rice paddy, a paddy 'unit' test was used. Paddy 'unit' set-up was completed 2 days prior to treatment and involved the use of a 13 cm×13 cm×10 cm plastic tub filled with soil to a depth of 5 cm. *Oryza sativa, Echinochloa crusgalli, Sagittaria pygmaea* and *Cyperus difformis*, each at 1–2 leaf stage, were 'transplanted' into the soil. The paddy units were then flooded such that the water level is 1.5 cm above the soil surface, this water depth was maintained throughout the experiment. Rates for the paddy test are based upon the surface area of the water in the paddy unit. Treatment involved pipetting a 0.7 cm$^3$ aliquot test sample, prepared as described above, into the water. Visual assessments were made 20 DAT by comparing treated to untreated plants and recording the observations using a scale of 0 to 100%, where 0 and 100 are equivalent to no phytotoxicity and complete kill, respectively.

TABLE II (species - see TABLE III)

| Compound No | Rate kg/HA | GM | ZM | CA | AR | IH | AT | SH | SV | BP | PD | EC | CE |
|---|---|---|---|---|---|---|---|---|---|---|---|---|---|
| 1 | 0.25 | 0 | 9 | 9 | 9 | 0 | 2 | 7 | 9 | 9 | 9 | 9 | 9 |
| 2A | 0.25 | 0 | 0 | 9 | 9 | 0 | 0 | 0 | 5 | 0 | 7 | 5 | 0 |
| 2B | 0.25 | 0 | 0 | 9 | 9 | 0 | 0 | 8 | 9 | 2 | 9 | 9 | 0 |
| 3A | 0.25 | 2 | 6 | 9 | 9 | 8 | 9 | 9 | 9 | 9 | 9 | 9 | 8 |
| 3B | 0.25 | 0 | 5 | 9 | 9 | 7 | 5 | 9 | 9 | 9 | 9 | 9 | 7 |
| 4A | 0.25 | 0 | 3 | 9 | 9 | 0 | 0 | 6 | 8 | 6 | 9 | 8 | 0 |
| 4B | 0.25 | 0 | 4 | 9 | 9 | 0 | 0 | 9 | 8 | 4 | 9 | 9 | 0 |
| 5 | 0.25 | 3 | 5 | 9 | 9 | 2 | 0 | 3 | 9 | 3 | 7 | 9 | 1 |
| 6 | 0.25 | 0 | 0 | 9 | 9 | 0 | 0 | 0 | 0 | 0 | 0 | 2 | 0 |
| 7A | 0.25 | 0 | 5 | 9 | 9 | 0 | 0 | 2 | 0 | 3 | 6 | 7 | 1 |
| 7B | 0.25 | 1 | 1 | 9 | 9 | 0 | 0 | 0 | 0 | 0 | 3 | 6 | 0 |
| 8A | 0.25 | 0 | 0 | 0 | 2 | 2 | 0 | 0 | 0 | 0 | 0 | 0 | 0 |
| 8B | 0.25 | 3 | 0 | 5 | 9 | 1 | 0 | 0 | 0 | 0 | 0 | 0 | 0 |
| 9 | 0.25 | 0 | 3 | 7 | 8 | 0 | 0 | 3 | 3 | 0 | 3 | 0 | 0 |
| 10A | 0.25 | 0 | 0 | 8 | 9 | 0 | 0 | 0 | 0 | 2 | 3 | 5 | 0 |
| 10B | 0.25 | 0 | 0 | 9 | 9 | 0 | 0 | 0 | 0 | 0 | 5 | 4 | 0 |
| 11A | 0.25 | 0 | 0 | 0 | 3 | 0 | 0 | 0 | 0 | 0 | 0 | 0 | 0 |
| 11B | 0.25 | 0 | 0 | 0 | 2 | 0 | 0 | 0 | 0 | 0 | 0 | 0 | 0 |
| 12A | 0.25 | 0 | 1 | 0 | — | 0 | 0 | 0 | 0 | 0 | 0 | 0 | 0 |
| 12B | 0.25 | — | 0 | 0 | 0 | 0 | 0 | 0 | 0 | 0 | 2 | 0 | 0 |

TABLE III

Abbreviations used for Test Plants

| | |
|---|---|
| GM | Soybean |
| ZM | Maize |
| CA | *Chenopodium album* |
| AR | *Amaranthus retroflexus* |
| BP | *Brachiaria platyphylla* |
| IH | *Ipomoea hederacea* |
| AT | *Abutilon theophrasti* |
| SH | *Sorghum halepense* |
| PD | *Panicum dichotomiflorum* |
| EC | *Echinochloa crus-galli* |
| CE | *Cyperus esculentus* |
| SV | *Setaria viridis* |

We claim:

1. A compound of formula I:

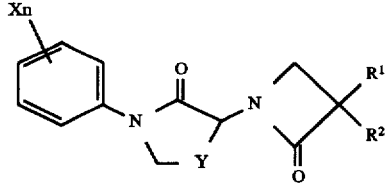

(I)

wherein n is 0 or an integer from 1 to 5;

X is halogen, nitro or cyano, or $C_{1-10}$ hydrocarbyl or $C_{1-10}$ hydrocarbyloxy, either of which may be substituted with one or more halogen atoms;

Y is $CH_2$, O or S; and $R^1$ and $R^2$ independently represent hydrogen, $C_{1-6}$ alkyl, $C_{1-6}$ haloalkyl $C_{2-6}$ alkenyl, $C_{2-6}$ alkynyl or halogen.

2. A compound of formula I according to claim 1, wherein n is an integer from 1 to 5.

3. A compound of formula I according to claim 1, wherein X is halogen, or $C_{1-10}$ hydrocarbyl or $C_{1-10}$ hydrocarbyloxy, either of which may be substituted with one or more halogen atoms.

4. A compound of formula I according to claim 1, wherein $R^1$ and $R^2$ independently represent $C_{1-6}$ alkyl, $C_{1-6}$ haloalkyl or halogen.

5. A compound of formula I according to claim 1 which is:

1-[1-(3-Trifluoromethoxyphenyl)pyrrolidin-2-one-3-yl]-3,3-dimethylazetidin-2-one;

1-[1-(3-Trifluoromethoxyphenyl)pyrrolidin-2-one-3-yl]-3-chloro-3-methylazetidin-2-one;

1-[1-(3-Trifluoromethoxyphenyl)pyrrolidin-2-one-3-yl]-3-chloromethyl-3-methylazetidin-2-one;

1-[1-(3-Trifluoromethoxyphenyl)pyrrolidin-2-one-3-yl]-3-bromo-3-methylazetidin-2-one;

1-[3-(3-Trifluoromethoxyphenyl)thiazolidin-4-one-5-yl]-3,3-dimethylazetidin-2-one;

1-[3-(3-Trifluoromethoxyphenyl)thiazolidin-4-one-5-yl]-3-bromo-3-methylazetidin-2-one;

1-[3-(3-Trifluoromethoxyphenyl)thiazolidin-4-one-5-yl]-3-chloromethyl-3-methylazetidin-2-one;

1-[3-(3-Trifluoromethoxyphenyl)thiazolidin-4-one-5-yl]-3-chloro-3-methylazetidin-2-one;

1-[3-(3-Trifluoromethoxyphenyl)oxazolidin-4-one-5-yl]-3,3-dimethylazetidin-2-one;

1-[1-(3-Trifluoromethoxyphenyl)oxazolidin-4-one-5-yl]-3-chloromethyl-3-methylazetidin-2-one;

1-[3-(3-Trifluoromethoxyphenyl)oxazolidin-4-one-5-yl]-3-bromo-3-methylazetidin-2-one;

1-[3-(3-Trifluoromethoxyphenyl)oxazolidin-4-one-4-yl]-3-chloro-3-methylazetidin-2-one;

1-[1-(3-Chloro-4-fluorophenyl)pyrrolidin-2-one-3-yl]-3,3-dimethylazetidin-2-one; or 1-[1-(3,5-Dichlorophenyl)pyrrolidin-2-one-3-yl]-3,3-dimethylazetidin-2-one.

6. A process of severely damaging or killing unwanted plants, which process comprises applying to the plants, or to the growth medium of the plants, a herbicidally effective amount of a compound of formula I according to claim 1.

7. A herbicidal composition, comprising as an active ingredient a compound of formula I according to claim 1, in admixture with a carrier comprising a solid or liquid diluent, and optionally a surface-active agent.

* * * * *